US 6,689,100 B2

(12) United States Patent
Connelly et al.

(10) Patent No.: US 6,689,100 B2
(45) Date of Patent: Feb. 10, 2004

(54) MICRODEVICE AND METHOD OF DELIVERING OR WITHDRAWING A SUBSTANCE THROUGH THE SKIN OF AN ANIMAL

(75) Inventors: Robert I. Connelly, Raleigh, NC (US); Ronald J. Pettis, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 19 days.

(21) Appl. No.: 09/971,145

(22) Filed: Oct. 5, 2001

(65) Prior Publication Data

US 2003/0069548 A1 Apr. 10, 2003

(51) Int. Cl.⁷ .............. A61M 5/00; A61M 5/32; A61M 35/00; A61K 9/22
(52) U.S. Cl. ............ 604/117; 604/115; 604/180; 604/890.1; 604/239; 604/274; 604/289
(58) Field of Search ................. 604/506, 513, 604/174, 180, 257, 272, 288.04, 46, 117, 890.1, 48, 507, 93.01, 103.01, 115, 19, 239, 264, 274, 289

(56) References Cited

U.S. PATENT DOCUMENTS

| | | | | |
|---|---|---|---|---|
| 3,688,764 A | * | 9/1972 | Reed | 600/556 |
| 3,964,482 A | | 6/1976 | Gerstel et al. | 128/260 |
| 4,473,083 A | * | 9/1984 | Maganias | 600/556 |
| 5,250,023 A | | 10/1993 | Lee et al. | 604/20 |
| 5,279,544 A | | 1/1994 | Gross et al. | 604/20 |
| 5,320,600 A | | 6/1994 | Lambert | 604/47 |
| 5,527,288 A | | 6/1996 | Gross et al. | 604/140 |
| 5,656,032 A | | 8/1997 | Kriesel et al. | 604/132 |
| 5,735,818 A | | 4/1998 | Kriesel et al. | 604/132 |
| 5,879,326 A | | 3/1999 | Godshall et al. | 604/51 |
| 5,957,895 A | | 9/1999 | Sage et al. | 604/181 |
| 5,997,501 A | | 12/1999 | Gross et al. | 604/65 |

(List continued on next page.)

FOREIGN PATENT DOCUMENTS

| | | | |
|---|---|---|---|
| CA | 2350307 | 1/2002 | A61B/5/15 |
| GB | 221394 A | 2/1990 | A61M/37/00 |
| WO | WO 96/37256 | 11/1996 | A61N/1/30 |
| WO | WO 97/48440 | 12/1997 | A61N/1/30 |
| WO | WO 97/48441 | 12/1997 | A61N/1/30 |
| WO | WO 00/12173 | 3/2000 | A61N/1/30 |
| WO | WO 00/74766 A1 | 12/2000 | A61M/37/00 |

OTHER PUBLICATIONS

Prausnitz, M. R. Drug Delivery by Electrical, Ultrasonic, and Microneedle Disruption of Biological Barriers. Abstracts of Papers of the American Chemical Society. Mar. 26, 2000; 176–MEDI.

McAllister, D. V.; Allen, M. G., and Prausnitz, M.R. Microfabricated Microneedles for Gene and Drug Delivery. Annual Review of Biomedical Engineering. 2000; 2:289–313.

(List continued on next page.)

Primary Examiner—Brian L. Casler
Assistant Examiner—Catherine S. Williams
(74) Attorney, Agent, or Firm—Robert E. West; Eric M. Lee

(57) ABSTRACT

A device for withdrawing or delivering a substance through the skin of a patient includes a body and a skin penetrating device having a plurality of skin penetrating members, such microneedles. The body includes a bottom surface having a first inner surface area supporting the skin penetrating members and a second outer surface having an adhesive for attaching the device to the skin. In one embodiment, the firs inner surface is spaced outwardly from the second outer surface when the device is attached to the skin. The inner surface can have a textured visually wettable surface, such as an etched surface, to provide a visual indication of leakage from the interface between the skin penetrating members and the skin.

39 Claims, 5 Drawing Sheets

U.S. PATENT DOCUMENTS

| | | | |
|---|---|---|---|
| 5,997,524 A | * 12/1999 | Burbank et al. | 604/506 |
| 6,050,988 A | 4/2000 | Zuck | 604/890.1 |
| 6,083,196 A | 7/2000 | Trautman et al. | 604/46 |
| 6,132,755 A | 10/2000 | Eicher et al. | 424/427 |
| 6,186,982 B1 | 2/2001 | Gross et al. | 604/132 |
| 6,219,574 B1 | 4/2001 | Cormier et al. | 604/20 |
| 6,230,051 B1 | 5/2001 | Cormier et al. | 604/20 |
| 6,256,533 B1 | 7/2001 | Yuzhakov et al. | 604/21 |
| 6,261,272 B1 | 7/2001 | Gross et al. | 604/272 |
| 6,322,808 B1 | 11/2001 | Trautman et al. | 424/448 |
| 6,558,361 B1 | 5/2003 | Yeshurun | 604/272 |
| 2002/0006355 A1 | 1/2002 | Whitson | 422/56 |

OTHER PUBLICATIONS

Lin, L. W. and Pisano, A. P. Silicon–Processed Microneedles, Journal of Microelectromechanical Systems. Mar 1999; 8(1): 78–84.

Ilic, L.; Gowrishankar, T.R.; Vaughan, T. E.; Herndon, T. O., and Weaver, J. C. Microfabrication of Individual 200 Mu M Diameter Transdermal Microconduits Using High Voltage Pulsing in Salicylic Acid and Benzoic Acid. Journal of Investigative Dermatology. Jan 2001; 116(1):40–49.

Henry, S.; McAllister, D. V,; Allen, M. G and Prausnitz, M.R. Microfabricated Microneedles: a Novel Approach to Transdermal Drug Delivery (vol. 87, p. 922, 1998), Journal of Pharmaceutical Sciences. Sep. 1999: 88(9):948.

Brazzle, J.; Papautsky, I., and Frazier, A.B. Micromachined Needle Arrays for Drug Delivery or Fluid Extraction —Design and Fabrication Aspects of Fluid Coupled Arrays of Hollow Metallic Microneedles, Ieee Engineering in Medicine and Biology Magazine. Nov. –Dec. 31 1999, 18(6)53–58.

* cited by examiner

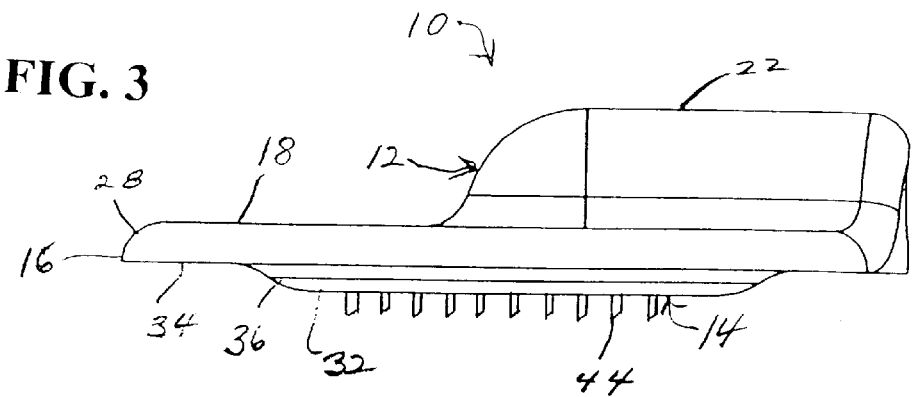
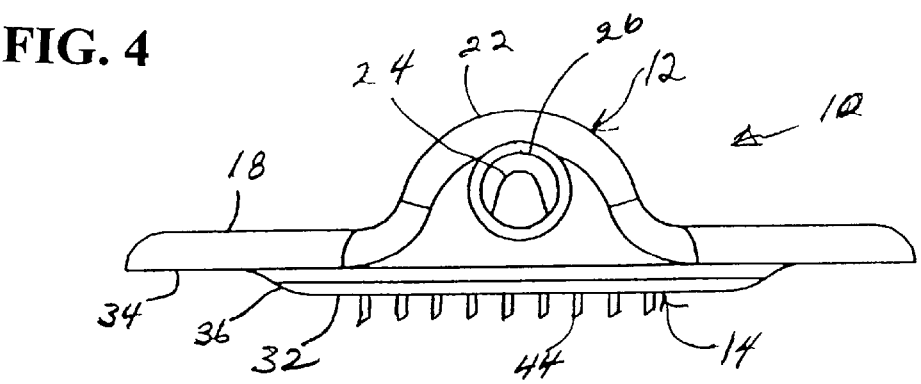
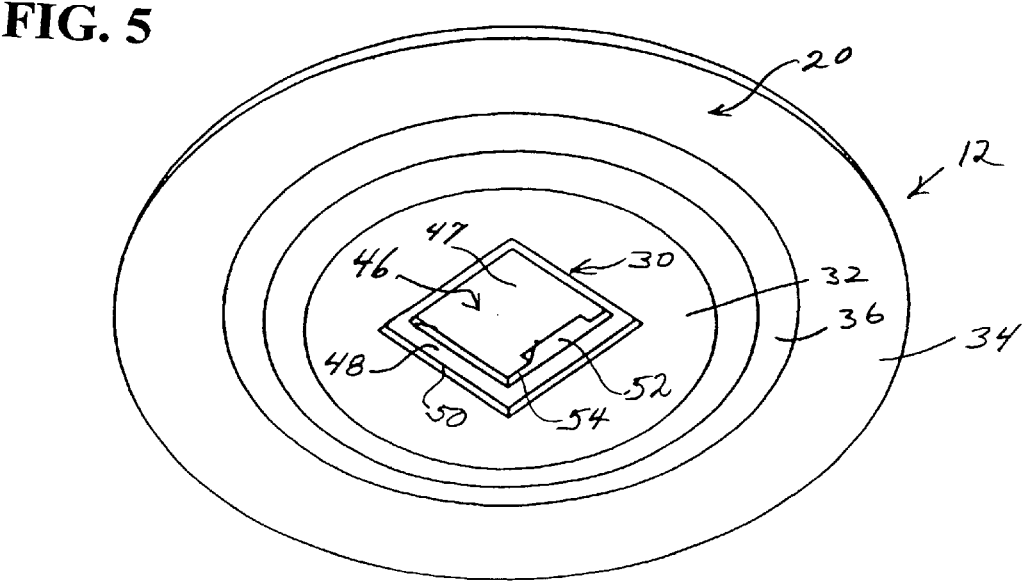

MICRODEVICE AND METHOD OF DELIVERING OR WITHDRAWING A SUBSTANCE THROUGH THE SKIN OF AN ANIMAL

FIELD OF THE INVENTION

The present invention relates to a microdevice and a method of delivering or withdrawing a substance through the skin of a patient, and in particular to a method and device for withdrawing or delivering a substance such as a drug intradermally to a patient. The invention also relates to a device for enhancing the penetration of a microneedle array.

BACKGROUND OF THE INVENTION

Various devices have been proposed for the intradermal sampling and delivering of substances such as pharmaceutical agents and drugs. Although subcutaneous sampling and delivery methods using a cannula are effective for many applications, the pain normally induced by the cannula has prompted the development of less painful delivery methods.

The skin is made up of several layers with the upper composite layer being the epithelial layer. The outermost layer of the skin is the stratum corneum that has well known barrier properties to prevent molecules and various substances from entering the body and analytes from exiting the body. The stratum corneum is a complex structure of compacted keratinized cell remnants having a thickness of about 10–30 microns. The stratum corneum forms a waterproof membrane to protect the body from invasion by various substances and the outward migration of various compounds.

The natural impermeability of the stratum corneum prevents the administration of most pharmaceutical agents and other substances through the skin. Numerous methods and devices have been proposed to enhance the permeability of the skin and to increase the diffusion of various drugs through the skin in order to be utilized by the body. According to some methods and devices, the delivery of drugs through the skin is enhanced by either increasing the permeability of the skin or increasing the force or energy used to direct the drug through the skin.

Other methods of sampling and delivering various substances through the skin form micropores or cuts through the stratum corneum. By piercing the stratum corneum and delivering a drug in or below the stratum corneum, many drugs can be effectively administered. In a similar manner, some substances can be extracted from the body through cuts or pores formed in the stratum corneum. The devices for piercing the stratum corneum generally include a plurality of micro-needles or blades having a length to pierce the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

The above-noted devices include micron-sized needles or blades and can be effective in delivering or sampling substances in the body. However, these needles and blades have a length of a few microns to a few hundred microns and typically do not penetrate the skin to a uniform depth. The natural elasticity and resilience of the skin often results in the skin being deformed by the needles rather than pierced. Therefore, when a microneedle array is pressed against the skin, the outermost needles penetrate the skin while the innermost needles do not penetrate the skin or only penetrate to depth less than the outermost needles.

As a result, the prior methods and devices for the intradermal sampling and administering of substances have exhibited limited success. Accordingly, a continuing need exists in the industry for an improved device for the sampling and administering of various drugs and other substances to the body.

SUMMARY OF THE INVENTION

A method and device for the intradermal sampling or delivery of a substance though the skin of a patient is provided. A method of manufacturing and assembling a device for intradermally delivering or withdrawing a substance through the skin of a patient is also provided. In particular, a method and apparatus for delivering a pharmaceutical agent, such as a drug or vaccine, into or below the stratum corneum of the skin to a sufficient depth where the pharmaceutical agent can be absorbed and utilized by the body is provided.

According to an exemplary embodiment of the invention, a microdevice interface is provided. The interface comprises a body having a top face and a bottom face. The bottom face has first and second surface areas. The first surface area is raised from the body with respect to the second surface area. A recess is defined in the first surface area on the bottom face. An opening is defined in the body for fluid flow for into and out of the body.

In a further embodiment, the recess is in fluid communication with the opening and the body and is adapted to receive a skin penetrating device.

In another exemplary embodiment, a device for intradermally delivering or withdrawing a substance through at least one layer of the skin of a patient is provided. The device comprises a body having a bottom face, a top face spaced from the bottom face, a side edge, and a width. The body has a height which extends between the top face and the bottom face and which is less than the width. A channel in the body extends from the side edge and has an axis which preferably extends substantially parallel to the bottom face. A skin penetrating device is coupled to the bottom face and is in fluid communication with the channel.

According to another exemplary embodiment, the device comprises a body having a top face, a bottom face and a side edge. The bottom face has a first surface area lying in a first plane and a second surface area lying in a second plane. The first surface area is spaced outwardly from the second surface area. At least one skin penetrating member extends from the first surface area of the bottom face and is oriented to penetrate the surface of the skin of the patient.

In another embodiment, the device comprises a body having a top face, a bottom face, and at least one side edge. A skin penetrating member is coupled to the body and extends outward from the bottom face. The bottom face has a first surface area surrounding the skin penetrating member. The first surface area also includes a leak indicator for indicating leakage from the device.

A method for delivery or withdrawal of a substance through at least one layer of the skin of a patient is also provided. The method comprises the steps of: providing a device having a body with a bottom face having at least one skin penetrating device, a first surface area surrounding the at least one skin penetrating device and lying in a first plane, and a second surface area lying in a second plane. The first surface area is spaced outwardly from the second surface area. The at least one skin penetrating device is positioned on a target site of the skin of the patient. Pressure sufficient for the skin penetrating device to penetrate the skin and for the second surface area to contact the skin is applied against the device. A substance is then delivered to the target site and to the patient.

Accordingly, a method and device for intradermal sampling or delivery of a substance is provided. The method and device can allow for penetration of the skin for sampling or delivering a substance through the skin, substantially without pain to the patient. The structure of the device provides a low profile and an increased comfort level to the patient. Additionally, the device may easily be manufactured as a single piece by injection molding.

The advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings in which:

FIG. 3 is a side elevational view of the device of FIG. 1 showing the skin penetrating members extending from the bottom face of the device;

FIG. 4 is an end view of the device of FIG. 1 showing the skin penetrating member bonded to the support as seen from the right side of FIG. 3;

FIG. 5 is a bottom perspective view of the support showing the recess of the support for receiving the skin penetrating device;

DETAILED DESCRIPTION OF THE PREFERRED EMBODIMENTS

Figure 1:
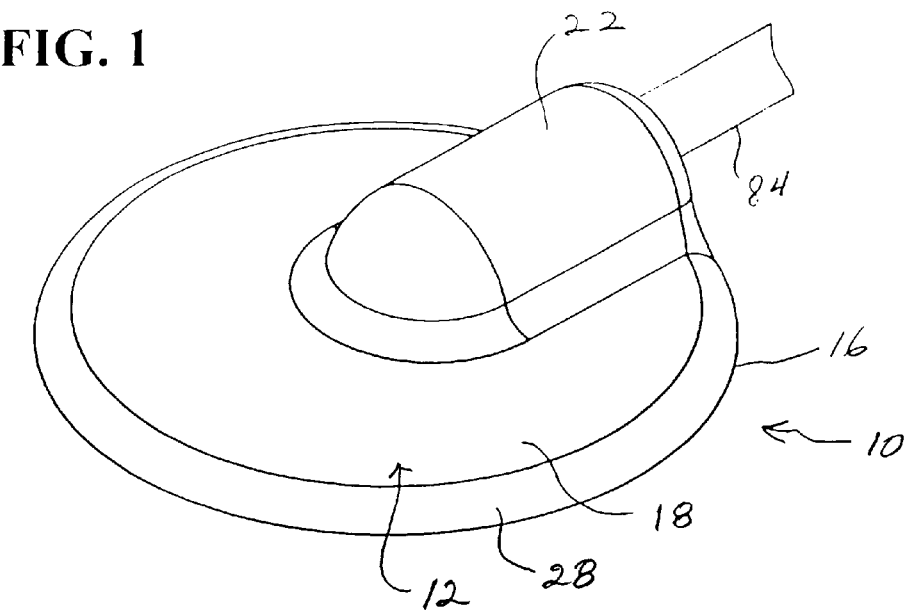
FIG. 1 is a perspective view of the device in accordance with a first embodiment of the invention for sampling or delivering a substance through the skin of a patient.

An intradermal device for sampling, monitoring or delivering a substance in or through the skin of a patient is provided. More particularly, a sampling, monitoring or delivery device and a method for sampling or administering a substance into or below the stratum corneum of the skin of a patient are provided.

As used herein, the term penetrate refers to entering a layer of the skin without passing completely through. Piercing refers to passing completely through a layer of the skin.

The device and method according to an embodiment of the present invention are suitable for use in administering various substances, including pharmaceutical agents, to a patient, and particularly to a human patient. As used herein, a pharmaceutical agent includes a substance having biological activity that can be delivered through the body membranes and surfaces, and particularly the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally to a patient include proteins, peptides and fragments thereof. The proteins and peptides can be naturally occurring, synthesized or recombinantly produced.

The device and method may also be used for withdrawing a substance or monitoring the level of a substance in the body. Examples of substances that can be monitored or withdrawn include blood, interstitial fluid or plasma. The withdrawn substances may then be analyzed for analytes, glucose, drugs and the like.

Generally, the device includes a body having a top surface and a bottom surface. An opening is provided in the body. The substance being delivered to or withdrawn from the patient passes through the opening. The bottom surface of the body contacts the patient. The bottom surface is provided with a raised area. At least one skin penetrating member is arranged in the raised area. The skin penetrating member is in fluid communication with the opening. In use, the device is arranged in a target site on the skin of the patient. When the device is attached to the skin of the patient, the raised area should result in a net pressure keeping the skin penetrating member pressed into the skin, thereby preventing leakage and ensuring efficiency of the delivery or the withdrawal of the substance to the patient. A leak detector can be provided on the bottom surface to indicate leakage of the device.

Referring to the drawings, an exemplary embodiment of the invention is now described. A device 10, having a body 12 and a skin penetrating device 14, is shown. The device 10 can be a monitoring device for monitoring a substance level in the body, a sampling device for withdrawing a sample from the body, or a delivery device for delivering a substance to the body, among others.

FIGS. 1–7 illustrate an embodiment of the invention for delivering or withdrawing a substance through the skin of a patient. Device 10 is particularly suitable for delivering or sampling a substance through the skin of a human patient, although the device is suitable for use with other animals.

Device 10 is constructed for penetrating selected layers of the dermis of a patient to a desired depth. The desired depth of penetration is usually determined by the substance being delivered or withdrawn and the target site. In one embodiment of the invention for delivering a pharmaceutical agent, the device is provided with at least one skin penetrating member having a length to pierce the stratum corneum, substantially without penetrating the layers of the dermis below the stratum corneum. In this manner, a substance can be delivered, absorbed and utilized by the body substantially without pain or discomfort to the patient.

Figure 2:
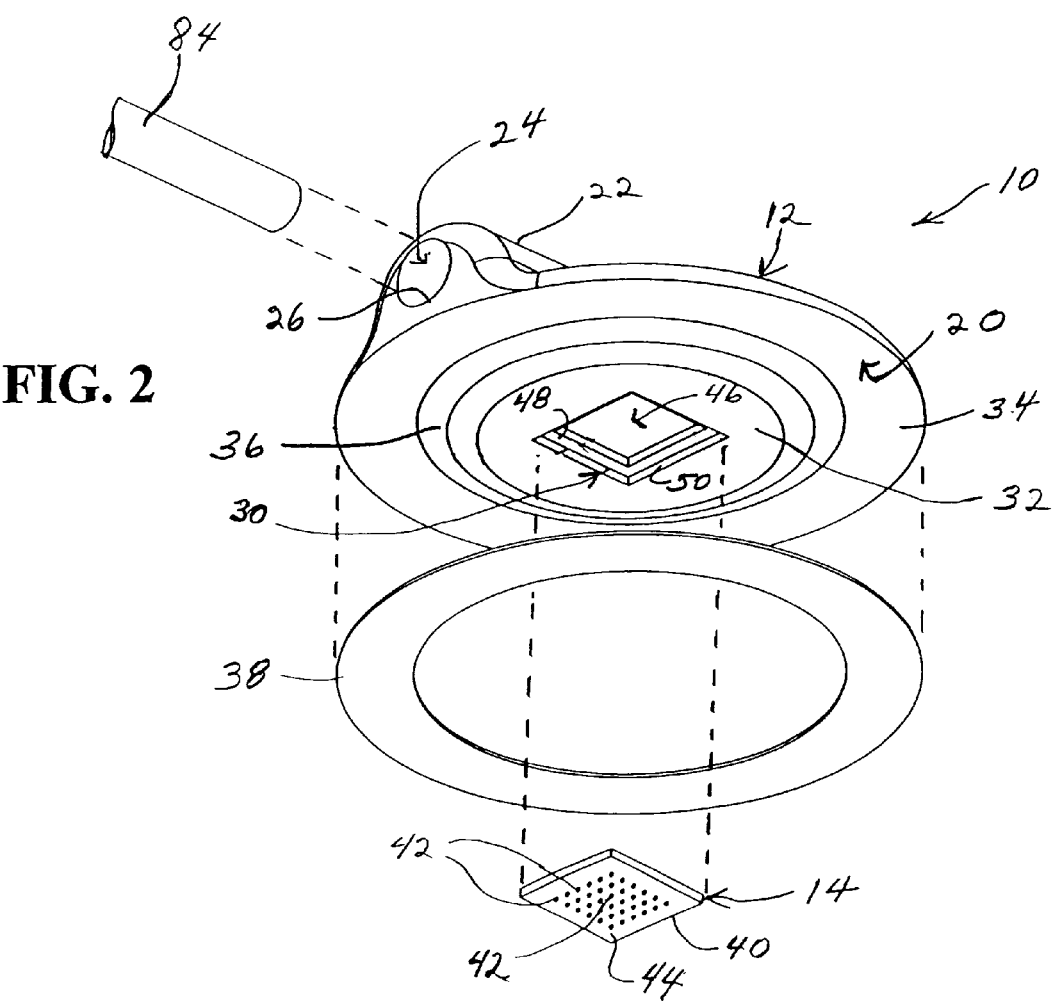
FIG. 2 is an exploded perspective view of the device of FIG. 1.

Referring to the drawings, body 12 preferably has a low profile to lie flat against the skin of a patient. The low profile provides for ease of attachment to the skin and less obstruction to the patient. The low profile can be achieved by reducing the height of the device. In the embodiment shown in FIG. 1, body 12 has a substantially circular disk shape, although in alternative embodiments, body 12 can have a non-circular shape or other shapes. Body 12 as shown in FIG. 1 has a circular outer side edge 16, a top face 18 and a bottom face 20. Outer side edge 16 preferably has a chamfered or rounded surface 28. A coupling member 22 is preferably integrally formed with body 12. Top face 18 may be otherwise substantially flat. Coupling member 22 defines a fluid channel 24 as shown in FIG. 2. Fluid channel 24 has an open inlet end 26. An axis of the fluid channel 26 preferably extends substantially parallel to a plane of body 12. In this manner, body 12 maintains a substantially flat, low profile configuration. Of course, other arrangements of the coupling member 22 and fluid channel 24 are possible to define an opening in the body 12.

Figure 7:
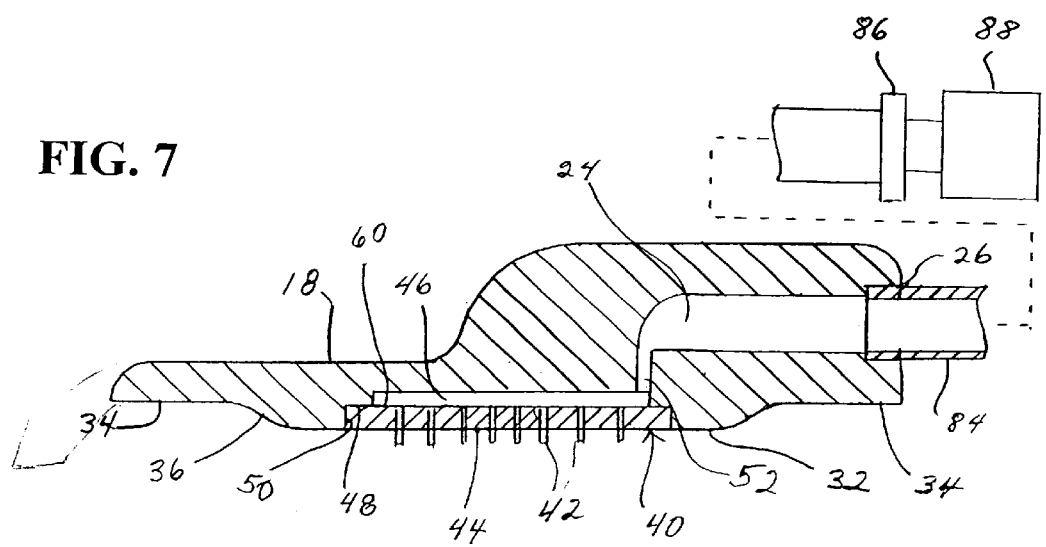
FIG. 7 is a cross-sectional side view showing the device in contact with the skin of a patient.

Bottom face 20 of body 12 includes a recess 30. Recess 30 is adapted to receive skin penetrating device 14. As shown in FIGS. 5 and 7, fluid channel 24 extends between inlet 26 and recess 30 for supplying a substance to skin penetrating device 14 or for directing a substance withdrawn from a patient to a suitable collection container.

Referring to FIGS. 2 and 5, bottom face 20 includes a first surface area 32 having recess 30 formed therein for supporting skin penetrating device 14. In preferred embodiments, first surface area 32 is a substantially flat planar surface and is centrally located in bottom face 20. In the embodiment illustrated, recess 30 is centrally located in bottom face 20 and is encircled by first surface area 32.

Bottom face 20 also includes a second surface area 34. First surface area 32 is preferably spaced radially outwardly from second surface area 34 with respect to a center axis of body 12. That is, first surface area 32 is raised with respect to second surface area 34. Preferably, second surface area 34 is a substantially flat, planar surface and first surface area 32 lies in a plane that is spaced outwardly from a plane of second surface area 34. In the embodiment illustrated, second surface area 34 is adjacent first surface area 32. Second surface area 34 may encircle first surface area 32 and define a continuous annular surface. In alternative embodiments, second surface area 34 can be discontinuous and may be formed as an element separate from first surface area 32.

As shown in FIGS. 3 and 4, first surface area 32 is substantially flat and lies in a plane substantially parallel to second surface area 34. In alternative embodiments, second surface area 34 can be at an incline with respect to first surface area 32 to define a substantially frustoconical shape. Second area 34 can also be inclined to form a convex surface or inclined to form a concave surface.

First surface area 32 is preferably connected to second surface area 34 by an inclined surface 36. Therefore, first surface area 32 can be spaced outwardly from second surface area 34 with respect to the plane of body 12, as mentioned above. The spacing between first surface area 32 and second surface area 34 can vary depending on the overall dimensions of device 10, the width of second surface area 34 in relation to the dimensions of first surface area 32 and the dimensions of skin penetrating device 14. Typically, first surface area 32 is spaced from second surface area 34 a distance of about 2.0 mm to about 5.0 mm. Preferably, first surface area 32 is spaced outwardly from second surface area 34 a distance to enable skin penetrating device 14 to penetrate the skin in a substantially uniform manner, as discussed hereinafter in greater detail.

Second surface area 34 may include an adhesive 38 applied thereto. Adhesive 38 is preferably a pressure sensitive adhesive capable of attaching device 10 to the surface of the skin of a patient as discussed hereinafter in greater detail. In the embodiment illustrated, adhesive 38 covers substantially the entire area of second surface area 34 and encircles first surface area 32. In this manner, second surface area 34 can be attached to the surface of the skin and form an annular fluid-tight seal encircling first surface area 32 and skin penetrating device 14. As mentioned above, adhesive 38 is preferably a coating of a suitable pressure sensitive adhesive and is applied directly to second surface area 32. In an alternative embodiment, adhesive 38 can be a double-faced adhesive tape having one face bonded to first surface area 32. Device 10 is preferably packaged with a release sheet covering adhesive 38 that can be removed immediately before use.

Preferably, second surface area 34 has a dimension sufficient to attach device 10 to the surface of the skin of a patient and to hold device 10 in place during the delivery or sampling of the substance, but still allow device 10 to be removed from the skin without unnecessary discomfort to the patient. The width of second surface area 34 can vary depending on the dimensions of device 10 and the spacing between first surface area 32 and second surface area 34.

In the embodiment discussed above, first surface area 32 has a planar configuration and lies in a plane that is spaced outwardly from and parallel to the plane of second surface area 34. In alternative embodiments, bottom face 20 of body 12 has a convex shape that forms a substantially continuous curved surface extending between first surface area 32 and second surface area 34. Additionally, the shape and dimensions of body 12 can vary depending on the substance being delivered or withdrawn from the patient, the dimensions of skin penetrating device 14 and the target site on the skin of the patient.

Body 12 is preferably made of a polymeric material by an injection molding process and may be formed as a single piece. Suitable polymers including polyethylene, polypropylene, polystyrene, polyesters, polyamines, polycarbonates, and copolymers thereof may be used. In one preferred embodiment, body 12 is made of a resilient polymeric material so that body 12 is sufficiently flexible to conform to the contour of the target area of the skin of the patient. Accordingly, the first and second surfaces areas 32, 34 of body 12 conform to the target site to provide a secure and comfortable attachment.

Referring now to FIGS. 2, 5 and 7, skin penetrating device 14 includes a base 40 having at least one skin penetrating members 42 extending from base 40. The skin penetrating members 42 are arranged to form an array of spaced apart rows and columns. In a preferred embodiment, base 40 has a substantially flat, planar bottom face 44 and the skin penetrating members 42 are substantially perpendicular to base 40. Typically, skin penetrating members 42 are hollow needles having an axial passage for carrying a substance to or from the skin of a patient.

As mentioned above, recess 30 is provided in bottom face 20 of body 12. Recess 30 should be dimensioned to receive skin penetrating device 14. As shown in FIGS. 2 and 7, recess 30 has a bottom surface 47 and defines a cavity 46 between bottom surface 47 and a top face 60 of base 40 of skin penetrating device 14. Recess 30 includes a ledge 48 having a substantially flat bottom surface extending around the perimeter of recess 30 for mating with top face 60 of base 40 of skin penetrating device 14. Ledge 48 is preferably substantially parallel to first surface area 32. Ledge 48 is defined by a sidewall 50 extending substantially perpendicular to first surface area 32. Side wall 50 defines a depth of ledge 48 with respect to first surface area 32.

In the embodiment shown in FIG. 7, ledge 48 is spaced from first surface area 32 by side wall 50 a distance corresponding substantially to the thickness of base 40 of skin penetrating device 14. In this manner, bottom face 44 of base 40 lies in substantially the same plane as first surface area 32. Consequently, skin penetrating members 42 extend from first surface area 32 a distance substantially equal to their length. In alternative embodiments, skin penetrating device 14 can be mounted in recess 30 so that bottom face 44 of base 40 is either recessed or spaced outwardly from first surface area 32.

Figure 8:
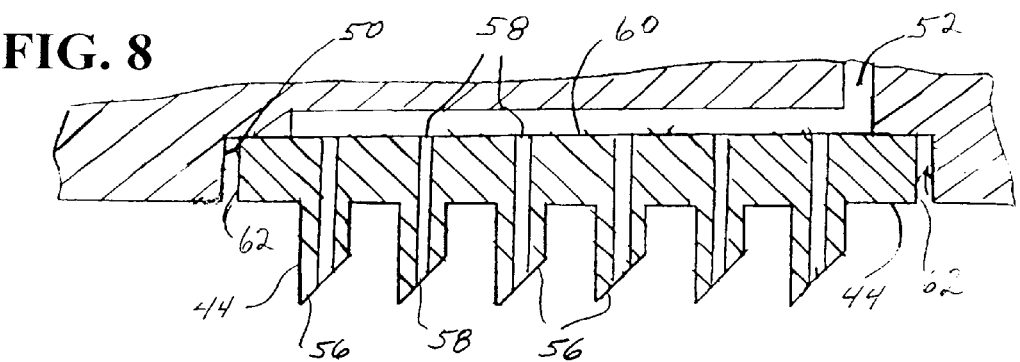
FIG. 8 is an enlarged cross-sectional side view of the skin penetrating device coupled to the support.
Figure 9:
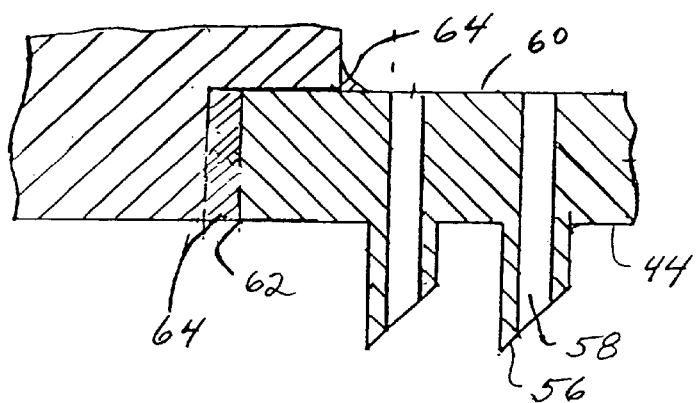
FIG. 9 is a cross-sectional view of the device of FIG. 8 showing the adhesive bonding the skin penetrating device to the support.

Skin penetrating device 14 is assembled to body 12 by positioning base 40 in recess 30 a shown in FIG. 8. Typically, base 40 has a dimension slightly less than the dimensions of recess 30 to provide a small gap between side wall 50 of ledge 48 and side edge 62 of base 40. An adhesive 64 is applied to the gap. The adhesive 64 then wicks between ledge 48 and top face 60 of base 40 due to surface tension of the adhesive 64 as shown in FIG. 9.

Figure 6:
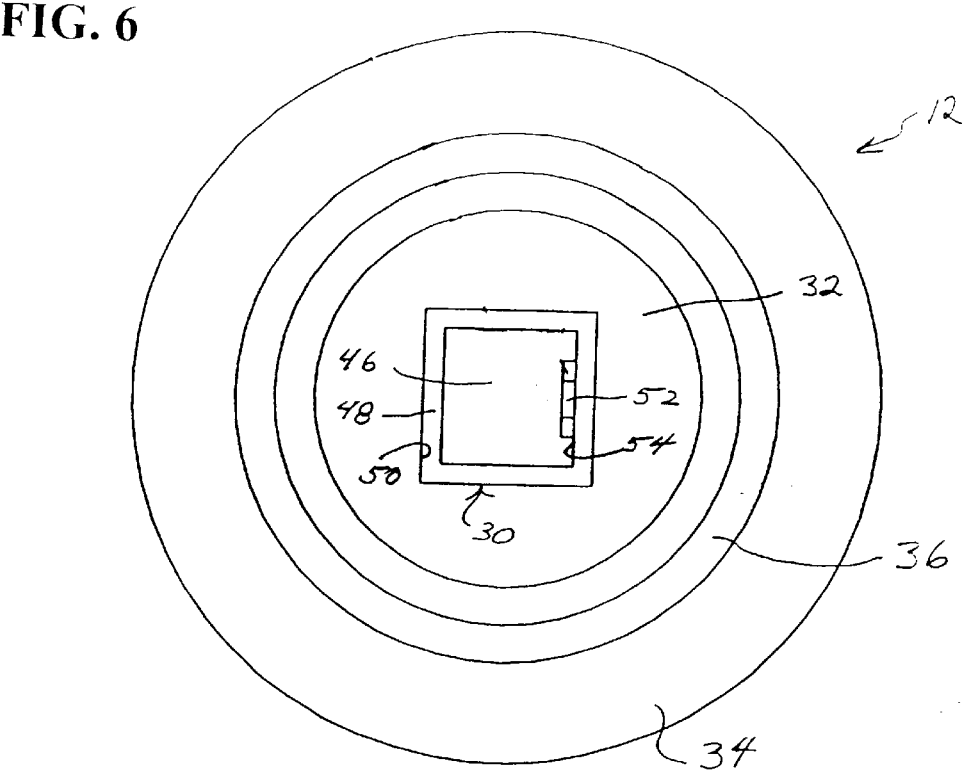
FIG. 6 is a bottom view of the device showing the recess for the skin penetrating device and a slot for supplying a substance to the skin penetrating device.

Referring now to FIGS. 5–7, cavity 46 is in fluid communication with fluid channel 24 via opening 52. Channel 24 terminates at opening 52. Opening 52 preferably has a longitudinal axis perpendicular to the plane of body 12 and is arranged along a side edge 54 of cavity 46. As shown in FIG. 7, cavity 46 should have a length and width to provide fluid communication between channel 24 and skin penetrating members 42. Cavity 46 should have a volume sufficient to allow the passage of a substance delivered to or withdrawn from skin penetrating members 44 while minimizing dead space to reduce the waste of the substance being delivered or withdrawn. Preferably, device 10 has a dead space of about 5 microliters or less.

In the embodiment illustrated, opening 52 is positioned to supply a substance along an edge of skin penetrating device 14, and at one end of cavity 46. In alternative, embodiments, opening 52 or another passage can be centrally oriented above the skin penetrating device or at other locations.

FIG. 8 illustrates an embodiment of skin penetrating device 14. Here, skin penetrating members 42 are needles having a longitudinal dimension and a beveled tip 56. An axial passage 58 extends between tip 56 and a top face 60 of base 40. In this embodiment, skin penetrating members 44 are integrally formed with base 40, although they may also be separate elements.

The skin penetrating members 42 may be arranged in any desired pattern on base 40. For example, skin penetrating members 42 may be arranged in an array formed by uniformly or non-uniformly spaced apart rows and columns. The number and spacing of the skin penetrating members can vary depending on the intended use. Typically, the skin penetrating device has about 10 to 100 skin penetrating members spaced apart a distance of about 0.05 mm to about 5 mm depending on the dimensions of the skin penetrating members. Skin penetrating members 42 can be spaced apart from each other a uniform distance and have a uniform length.

Skin penetrating device 14 and skin penetrating members 42 can also be made from various materials. Skin penetrating members 42 of skin penetrating device 14 may be made of silicon by suitable silicon etching or micromachining steps. In further embodiments, the skin penetrating members and/or base 40 of device 14 are made from stainless steel, tungsten steel, and alloys of nickel, molybdenum, chromium, cobalt and titanium. Alternatively, the skin penetrating members 42 and/or the base 40 of device 14 can be made of ceramic materials, polymers and other non-reactive materials. The base 40 and skin penetrating members 42 can be made from materials which differ from each other.

The length of skin penetrating members 42 is selected to achieve the desired depth of penetration in the skin. The length and thickness of the skin penetrating members 42 are usually determined based on the substance being administered or withdrawn, as well as the thickness of the skin in the location where the device is to be applied. Generally, the skin penetrating members have a length, as measured from the base to the tip of the member, of about 50 microns to about 4,000 microns and preferably, about 250 microns to 1500 microns. The skin penetrating members can be microneedles, microtubes, solid or hollow needles, lancets and the like. In one embodiment, the skin penetrating members are about 30-gauge to about 50-gauge needles, having a length of about 500 microns to about 1500 microns. The skin penetrating members may have a substantially square cross-sectional shape. Alternatively, the skin penetrating members can be triangular, cylindrical, pyramid-shaped or flat blades.

Skin penetrating device 14 can have various dimensions and shapes as necessary to achieve the desired result. In one embodiment, skin penetrating device 14 is about 1 cm$^2$ to about 10 cm$^2$. In further embodiments, skin penetrating device 14 can have a width and length of about one centimeter to about five centimeters. Base 40 can have a thickness of about 200 to 400 microns, and typically about 250 microns.

Generally, when the device is used as a delivery device, a pharmaceutical agent or drug solution is introduced into the opening in the body by a syringe or other fluid dispensing device. In alternative embodiments, a dried or lyophilized drug or pharmaceutical agent can be provided on the outer or inner surfaces of the skin penetrating members or in the axial passages of the skin penetrating member. A diluent such as distilled water or saline solution can then be injected through the opening and the axial passage of the skin penetrating members to dissolve and reconstitute the drug or pharmaceutical agent and then deliver the drug to the patient.

Figure 10:
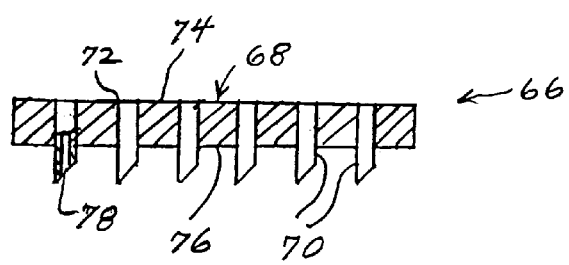
FIG. 10 is a side view in partial cross-section of the skin penetrating device in a second embodiment.
Figure 11:
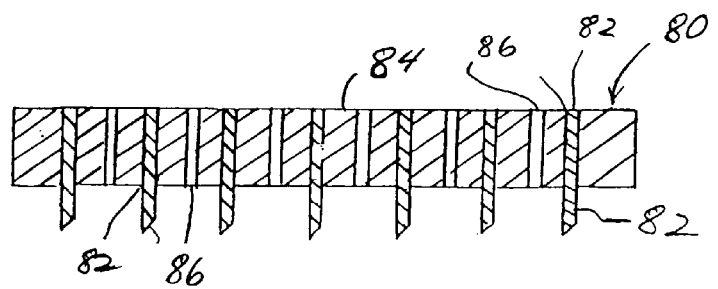
FIG. 11 is a side view in partial cross section of the skin penetrating device in another embodiment of the invention.

FIG. 10 shows an alternative embodiment of a skin penetrating device 66 having a base 68 and a plurality of skin penetrating members 70. In this embodiment, base 68 is formed with a plurality of holes 72 extending between a top face 74 and a bottom face 76 thereof. Skin penetrating members 70 are shown as hollow needles having an axial passage 78. The skin penetrating members 70 are fitted into respective holes 72. In further embodiments shown in FIG. 11, a skin penetrating device 80 includes a plurality of solid needles 82 extending from a base 84. A plurality of holes 86 are provided between adjacent needles 82 to supply a substance to the target area of the skin.

Device 10 may be connected to a supply tube 84 to supply a substance to be delivered to a patient. This connection can be achieved via coupling portion 22. As shown in FIG. 7, supply tube 84 can include at one end a suitable coupling 86 for coupling to coupling portion 22. Coupling 86 can be a luer type fitting or other threaded coupling, that coupling portion 22 is adapted to accept. The other end of supply tube 84 can be connected to a supply device 88. Supply device 88 may be a syringe, a unit dose delivery device, a suitable metering pump or infusion device for delivering a substance to device 10 at a controlled rate.

Figure 12:
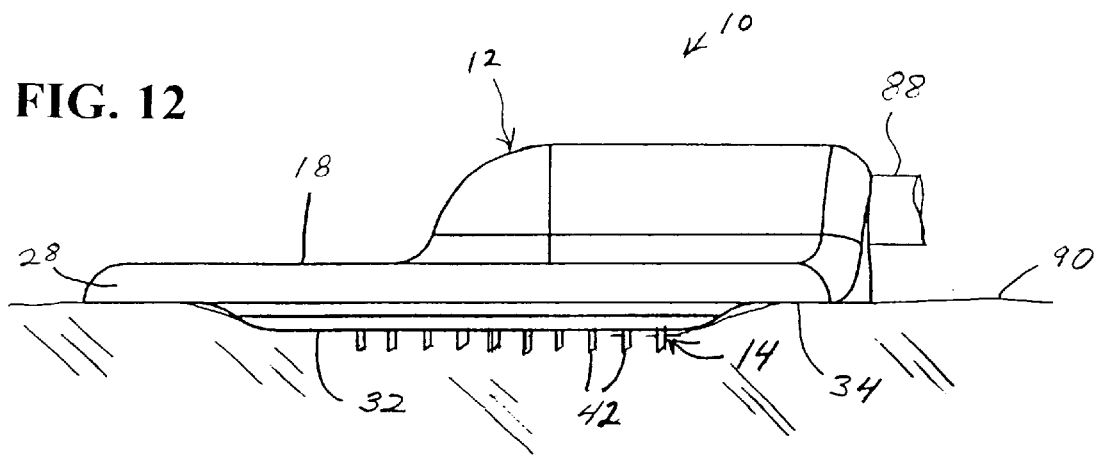
FIG. 12 is a side view of the device of FIG. 1 showing the penetration of skin by the device.

Turning now to FIG. 12, a method for delivering or withdrawing a substance through the skin is described. Device 10 is positioned in a target site on the surface of a patient's skin 90. Body 12 is pressed downwardly against skin 90 with a pressure sufficient to cause skin penetrating members 42 to penetrate the layers of skin 90. The depth of penetration is dependent upon the length of skin penetrating members 42, the spacing of the skin penetrating members 42, and the dimensions of body 12. Body 12 should be pressed downwardly until second surface area 34 and adhesive 38 contact skin 90 such that body 12 is attached to skin 90.

As discussed above, first surface area 32, on which at least one skin penetrating member is arranged, is spaced outwardly from second surface area 34. The skin of a patient has elastic properties that resist penetration by the skin penetrating member. The skin is typically stretched by the skin penetrating members 42 until the skin is taunt before the skin penetrating members penetrate the skin. By spacing the skin penetrating members 42 outwardly from the plane of second surface area 34, a penetrating pressure can be applied to the skin penetrating device 14 before second surface area 34 contacts the skin. This promotes uniform penetration of the skin by each of the skin penetrating members. Consequently, when second surface area 34 is attached to skin 90, a pressure is constantly applied to skin penetrating members 42. The spacing between first surface area 32 and second surface area 34 is a distance sufficient so that a substantially constant and uniform pressure is applied by the skin penetrating members 42 to the skin when second surface area 34 is attached to the skin. Preferably, this spacing provides a sufficient penetrating pressure without interfering with the attachment of the second surface area 34 to the skin. A substance is supplied to supply tube 88, which is then fed to skin penetrating device 14 for delivery to the patient. In alternative embodiments, a substance is withdrawn from the patient in a similar manner.

Figure 13:
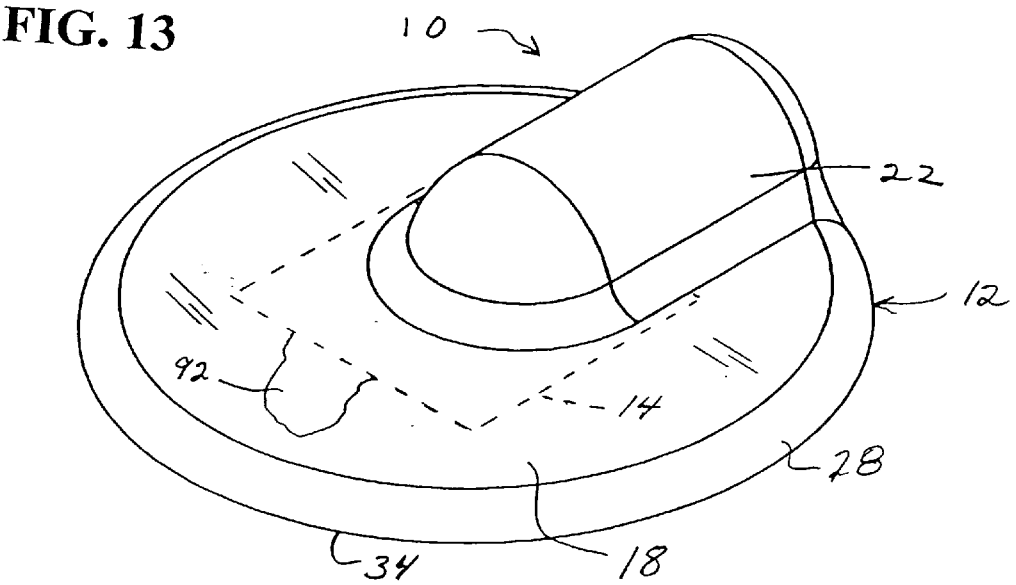
FIG. 13 is a top perspective view of the device showing the leak detection system from the delivery target area.

In a further embodiment of the present invention, the device 10 can be provided with a leak detector. The leak detector may detect leakage between the skin of the patient and the device 10. The leak detector preferably provides a visual indication of leakage. The leak detector may be any surface or surface treatment that provides a visual indication of leakage, such as when the surface is contacted by the substance being delivered or overdrawn via device 10. An example of a leak detector is illustrated in FIG. 13. Here, the first surface area 32 of body 12 is provided with a matte surface texture. This gives first surface area 32 a frosted appearance. The matte texture can be created by a plurality of microscratches or microtexture. The first surface area 32 and the microscratches wick leaking substances into the interstices of the first surface area 32 to provide a readily visible area where the leaking substance contacts the surface, thus indicating leakage.

For example, device 10 is placed against the skin of a patient as previously discussed so that skin penetrating members 42 penetrate the skin in the target site. Body 12 is preferably made from a transparent or translucent material having sufficient clarity so that the leak detector is visible through top face 18 of body 12. A substance to be delivered to or withdrawn from the patient is supplied through channel 24 to skin penetrating device 14 and to the target area of the skin. In the event of leakage at the interface between skin penetrating device 14 and the target site of the skin, the leaking substance is drawn into the interstices of the leak detector to provide a visual indication of leakage, depicted as 92 in FIG. 13. Adhesive 38 may be provided around the circumference of body 12 on second surface area 34 to contain any leaking substance.

The device of the invention can remain in contact with the skin for sufficient time to withdraw from or deliver to the patient the desired substances. The length of time the device 10 is required to be attached is usually dependent on the substance being delivered or withdrawn, the volume of the substance, the target area on the skin, the depth of penetration and the number and spacing of skin penetrating members.

Accordingly, a method and device for withdrawing or delivering a substance intradermally to a patient is provided. The device of the invention can be used as a disposable, single-use device. The device can be sterilized and can be stored in a suitable sterile package. Preferably, a cover having a release coating is provided on the bottom surface to protect the skin penetrating device and the adhesive coating. The release coating enables the cover to be easily separated from the adhesive coating. The method and device can be used safely and effectively for intradermal delivery of a pharmaceutical agent or other substance. The device is particularly suitable for introducing a vaccine intradermally for efficiently delivering a small amount of a vaccine antigen. The length, width and spacing of the microneedles can vary depending on the pharmaceutical agent being administered or required to penetrate the stratum corneum to the optimum depth for the specific pharmaceutical agent being administered. When delivering a vaccine, the microneedles are dimensioned to target the optimum intradermal delivery site to promote the desired immune response.

While various embodiments have been chosen to illustrate the invention, it will be appreciated by those skilled in the art that various additions and modifications can be made to the invention without departing from the scope of the invention as defined in the appended claims. For example, the body of the device may be made as an integral one-piece unit. In alternative embodiments, the body can be made from separately molded sections or pieces and assembled together. The molded sections can be assembled using an adhesive, by welding, or by the use of mechanical fasteners. Additionally, any number of skin penetrating members and devices may be provided on the device.

What is claimed is:

1. A device for intradermally delivering or withdrawing a substance through at least one layer of the skin of a patient, said device comprising:

a body having a bottom face, a top face spaced from said bottom face, a side edge, and a width, said body having a height extending between said top face and said bottom face that is less than said width, said body defining a channel extending longitudinally from said edge, substantially parallel to said bottom face;

a skin penetrating device coupled to said bottom face and being in fluid communication with said channel, said skin penetrating device comprises a base and a plurality of skin penetrating members arranged in an array and extending outwardly from said base; and wherein said body defines a recess in said bottom face, said recess being dimensioned to receive said skin penetrating device, said skin penetrating device being mounted in said recess, and wherein said channel is in fluid communication with said recess for supplying the substance to said skin penetrating device.

2. The device of claim 1, wherein said base has a substantially planar bottom face and said skin penetrating device is mounted in said recess whereby said bottom face of said base is oriented in substantially the same plane as said bottom face of said body.

3. The device of claim 1, wherein said bottom face of said body has a substantially planar first surface area and a substantially planar second surface area, the second surface area being arranged adjacent said first surface area, wherein said first surface area is spaced outwardly from said second surface area and said skin penetrating device is arranged in said first surface area.

4. The device of claim 3, wherein said second surface area surrounds said first surface area and an adhesive layer is provided on said second surface area for attaching said device to the skin of said patient.

5. The device of claim 3, wherein said second surface area includes an adhesive for attaching said second surface area to the skin of said patient, whereby said skin penetrating device contacts said skin with a pressure sufficient to penetrate said skin.

6. The device of claim 3, wherein said first surface area of said bottom face includes a leak detector for indicating leakage of said substance from an interface between said skin penetrating device and said skin of said patient.

7. The device of claim 6, wherein said leak detector comprises a surface texture on said first surface area for visually indicating contact of said first surface area with a liquid.

8. The device of claim 7, wherein said body is made of a material having a clarity sufficient to view said leak detector through said top surface of said body.

9. The device of claim 1, wherein said body is made from a resilient plastic material.

10. The device of claim 1, wherein said skin penetrating device includes a base and a plurality of skin penetrating members arranged in an array on said base, said skin penetrating members have a length of about 50 microns to about 4,000 microns.

11. A device for intradermally delivering or withdrawing a substance through at least one layer of the skin of a patient, said device comprising:

a body having a top face and a bottom face, said bottom face having a first surface area lying in a first plane and a second surface area lying in a second plane, said first surface area being spaced outwardly from said second surface area; and a skin penetrating device extending from said first surface area of said bottom face and being oriented to penetrate the surface of said skin of said patient; and wherein said bottom face includes a leak detector for indicating leakage of said substance from between said skin penetrating device and said skin of said patient.

12. The device of claim 11, wherein said second surface area surrounds said first surface area.

13. The device of claim 11, wherein an adhesive is arranged in said second surface area for attaching said device to said skin of said patient.

14. The device of claim 13, wherein said first surface area is spaced outwardly from said second surface area a distance to apply a pressure to said skin sufficient to cause said skin penetrating device to penetrate said skin when said second surface area is attached to said skin.

15. The device of claim 11, wherein said skin penetrating device comprises a base and a plurality of skin penetrating members arranged in an array and extending outwardly from said base.

16. The device of claim 15, wherein said skin penetrating members have a length of about 50 microns to about 4,000 microns.

17. The device of claim 11, wherein said leak detector comprises a visible surface texture on said first surface area for visualizing contact of said bottom face of said first surface area with the substance, and wherein said visible surface texture is visible through said top face.

18. The device of claim 17, wherein said visible surface texture comprises a plurality of microscratches on said first surface area of said bottom face.

19. The device of claim 17, wherein said visible surface texture comprises an etched surface on said first surface area of said bottom face.

20. A device for intradermally delivering or withdrawing a substance through at least one layer of the skin of a patient, said device comprising:

a body having a top face and a bottom face; and at least one skin penetrating member coupled to said body and extending outwardly from said bottom face;

said bottom face having a first surface area surrounding said at least one skin penetrating member, said first surface area having a leak detector for indicating the presence of a substance in contact with said bottom face.

21. The device of claim 20, wherein said leak detector comprises a visual leak indicator on said first area of said bottom face.

22. The device of claim 21, wherein said top surface is transparent such that said visual leak indicator is visible.

23. The device of claim 21, wherein said visual leak indicator comprises a plurality of microscratches in said first surface area.

24. The device of claim 21, wherein said visual leak indicator comprises an etched surface on said first area.

25. The device of claim 21, wherein said visual leak indicator encircles said skin penetrating member.

26. A method of delivering or withdrawing a substance through at least one layer of the skin of a patient, said method comprising the steps of:

providing a device having a body with a bottom face, at least one skin penetrating device arranged on said bottom face, said bottom face including a first surface area arranged in a first plane and surrounding said skin penetrating device and a second surface area arranged in a second plane, said first surface area being spaced outwardly from said second surface area and having a leak detector;

positioning said skin penetrating device on a target site of said skin of said patient;

applying a pressure against said device sufficient for said skin penetrating device to penetrate said skin and for said second surface area to contact said skin; and delivering a substance to or withdrawing a substance from said target site of said patient.

27. The method of claim 26, further comprising adhesively attaching said second surface area to said skin.

28. The method of claim 26, wherein said second surface area surrounds said first surface area.

29. The method of claim 28, wherein said skin penetrating members have a length of about 50 microns to about 4,000 microns.

30. The method of claim 26, wherein said skin penetrating device comprises a base and an array of a plurality of skin penetrating members extending from said base.

31. The method of claim 30, wherein said base has a planar bottom face and said bottom face of said base is oriented in said first plane.

32. The method of claim 26, wherein said device has an internal channel extending between an inlet and said at least one skin penetrating device, said method comprising supplying a substance through said internal channel to said skin penetrating device.

33. The method of claim 26, wherein said leak indicator comprises a plurality of microscratches on said first surface area.

34. The method of claim 26, wherein said leak indicator comprises an etched surface on said first surface area.

35. A microdevice interface, comprising:
- a body having a top face and a bottom face, said bottom face having a first surface area and a second surface area, said first surface area being raised from said body with respect to said second surface area;
- a recess defined in said first surface area said recess having a height that is less than a width;
- an opening defined in said body for fluid flow into and out of said body, said opening being in fluid communication with said recess;
- wherein said opening and said recess are in fluid communication via a second opening, said second opening being perpendicular to a plane of the device.

36. The interface of claim 35, further comprising a skin penetrating device arranged in said recess.

37. The interface of claim 35, wherein said second surface area includes an adhesive for attaching said second surface area to the skin of said patient, whereby said skin penetrating device contacts said skin with a pressure sufficient to penetrate said skin.

38. The interface of claim 35, wherein said first surface area is spaced outwardly from said second surface area a distance to apply a pressure to said skin sufficient to cause said skin penetrating device to penetrate said skin when said second surface area is attached to said skin.

39. The interface of claim 35, wherein said second surface area is arranged around a circumference of said bottom face.

* * * * *